United States Patent [19] [11] 3,974,159
Decker et al. [45] Aug. 10, 1976

[54] MANUFACTURE OF DERIVATIVES OF MALONDIALDEHYDE

[75] Inventors: Martin Decker, Ludwigshafen; Willibald Schoenleben, Heidelberg; Herbert Toussaint; Hewig Hoffmann, both of Frankenthal, all of Germany

[73] Assignee: BASF Aktiengesellschaft, Ludwigshafen (Rhine), Germany

[22] Filed: Apr. 28, 1975

[21] Appl. No.: 572,135

[30] Foreign Application Priority Data
May 20, 1974 Germany.............................. 2424373

[52] U.S. Cl..................... 260/247.5 R; 260/293.87; 260/566 R; 260/566 AE
[51] Int. Cl.².............. C07C 119/00; C07C 131/00
[58] Field of Search... 260/566 R, 566 AE, 247.5 R, 260/293.87

[56] References Cited
OTHER PUBLICATIONS
Arnold et al., Collect. Czech. Chem. Commun. 23, 452 (1958).

*Primary Examiner*—Gerald A. Schwartz
*Attorney, Agent, or Firm*—Johnston, Keil, Thompson & Shurtleff

[57] ABSTRACT
Compounds of the general formula

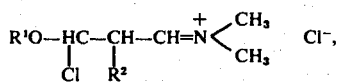

which may be used in place of malondialdehyde in synthesis reactions are obtained in a one-step reaction form dimethylformamide, phosgene and an alkyl vinyl ether.

3 Claims, No Drawings

MANUFACTURE OF DERIVATIVES OF MALONDIALDEHYDE

Functional derivatives of malondialdehyde, eg. its acetals, are required for the synthesis of pyrimidines, pyrazoles and isoxazoles. Eg., according to German Patent 1,117,587 a derivative of malondialdehyde can be reacted with guanidine to give 2-aminopyrimidine, which is used as an intermediate for sulfadiazine, a therapeutically used sulfonamide.

An inexpensive method of manufacture of such derivatives of malondialdehyde is the formylation of vinyl ethers or of enolethers generally. This method is a variant, described by Arnold and Sorm (Collect. Czech. Chem. Commun. 23 (1958), 452), of the Vilsmeier-Haack aldehyde synthesis. The formylating agent used is "dimethylformamide chloride" obtainable from dimethylformamide and phosgene:

This agent reacts with a vinyl ether essentially as follows:

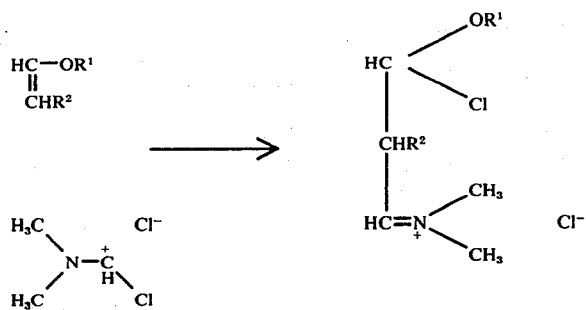

It is known that instead of the vinyl ethers, the corresponding α-chloroethers or acetals may be used. The compounds obtained may be regarded as functional derivatives of malondialdehyde or of a 2-substituted malondialdehyde.

Hitherto, the two reactions (1) and (2) have been carried out in succession in the presence of solvents, the first reaction at room temperature or below and the second reaction at from 30° to 75°C. Both reactions are exothermic. The purity of the compounds thus obtained is not very high. The compounds contain resinous impurities and when converted further to the heterocyclic compounds mentioned initially give an overall yield in these of at most 80 percent. The original method, also carried out in several successive steps, in most cases uses phosphorus oxychloride instead of phosgene and, apart from the economic aspects, is also rather unsatisfactory.

It is an object of the present invention to provide a process which gives derivatives of malondialdehyde in as high a yield as possible.

We have found that derivatives of malondialdehyde, of the general formula

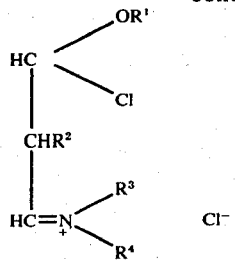

in which $R^1$ is alkyl of, eg., up to 8 carbon atoms, $R^2$ is hydrogen or alkyl or alkoxy, eg. of up to 20 carbon atoms, and $R^3$ and $R^4$ are identical or different, generally short-chain, alkyl of up to 4 carbon atoms or, together with the nitrogen to which they are attached, are a heterocyclic ring of up to 7 members, are obtained in (1)

almost quantitative yield by reaction of phosgene with a dialkylformamide of the general formula (2)

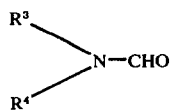

to give the dialkylformamide chloride and reaction of the dialkylformamide chloride with an enol ether (vinyl ether) of the general formula $R^2$—CH=CH—$OR^1$ wherein $R^1$, $R^2$, $R^3$ and $R^4$ have the above meanings, provided that the reactions are allowed to take place simultaneously.

"Simultaneously" in the present invention means concurrently, in the same reaction space.

The reactions are preferably carried out continuously. In a variant which has proved particularly successful, at least 50%, and in particular at least 80%, of the total conversion take place in a reaction space with controllable and, if appropriate, complete back-mixing and the remaining conversion (if any) takes place in a reaction space with little, or negligible, back-mixing.

The reaction temperature is in general from 40° to 100°C, especially from 55° to 75°C, in the first reaction space; in the second reaction space, it is in general within the same range but it is possible, and at times desirable, that here it should eg. be higher, say from 65° to 90°C.

The reaction normally takes place under essentially atmospheric pressure, provided there are not excessively volatile reactants (eg. vinyl methyl ether) present, and preferably takes place in the reaction mixture per se, ie. without added solvents which do not participate in the reaction. However, it is possible to carry out the reaction in the presence of, eg., benzene, toluene or chloroform.

Normally it is not necessary to deviate from the stoichiometrically required amounts of starting materials, but the success of the reaction is not dependent on precise observation of the stoichiometric proportions. A suitable composition of the reaction mixture is, eg., a molar ratio of dialkylformamide:phosgene:vinyl ether of (from 0.5 to 1.5):(from 0.5 to 1.5):(from 0.5 to 1.5).

Examples of dialkylformamides for carrying out the process are dimethylformamide, diisobutylformamide, N-formylpiperidine and N-formylmorpholine. In general dimethylformamide is preferred, solely for cost reasons; the radicals present on the nitrogen are in general immaterial as regards the usefulness of the malondialdehyde derivative in chemical reactions.

Examples of vinyl ethers or enol-ethers which may be used are vinyl isobutyl ether, vinyl methyl ether, 1,2-dimethoxyethylene and propenyl ethyl ether.

Reaction of the malondialdehyde derivative manufactured according to the invention with, eg., guanidine gives 2-aminopyrimidine or 2-amino-5-alkyl-pyrimidines in yields of up to 97% of theory.

The result achieved by the invention is unexpected. The simultaneous combination of the three reactants does not result in increased resinification, as might have been expected because of vinyl ethers being sensitive to polymerization by acid compounds; on the contrary, the quality of the product is improved, as shown by the yield of subsequent products. It should be mentioned that the derivatives of malondialdehyde which are concerned are very sensitive and therefore very difficult to purify; it is extremely important that they should be prepared by a synthesis which proceeds as smoothly as possible, since, eg., purification by distillation is in general not feasible.

A further advantage of the process is that if the reactants are brought together simultaneously, and in particular continuously, deposition of solid (salt-like) dialkylformamide chloride is avoided. If the reaction temperature is sufficiently high, the reaction with the vinyl ether evidently proceeds more rapidly than the separating-out of the salt. Accordingly, the mixture remains fluid and a solvent or diluent is superfluous.

EXAMPLE 1

Per hour, 7.3 kg of dimethylformamide (molecular weight 73), 10.0 kg of vinyl isobutyl ether (molecular weight 100) and, through a separate line, 10 kg of phosgene (molecular weight 99) are fed in continuously at a low point of a tubular loop reactor of 8 l capacity. The carbon dioxide formed during the reaction rises and ensures rapid circulation on the principle of the air-lift pump. The reaction temperature is kept at 70°C by a heat exchanger. A branch is provided in the upper arc of the loop reactor. From there the reacting gas-liquid mixture passes into a finishing reactor at the same rate as raw materials are introduced.

The finishing reactor consists of a column, filled with Raschig rings, which has a free volume of 65 l and is run as a liquid phase reactor. The reaction temperature is again 70°C. The finishing reactor gives 22.9 kg/hour of a reaction product which is regarded as the desired malondialdehyde derivative.

To manufacture 2-aminopyrimidine, 19.6 kg of guanidine hydrochloride and 12 kg of NaOH are dissolved in 60 kg of methanol, whereupon sodium chloride precipitates. Without filtering off the latter, the 22.9 kg of malondialdehyde deivative, obtained above, are run in at 65° in the course of one hour, and the batch is stirred for a further hour at the same temperature. After conventional working-up, 9.2 kg of pure 2-aminopyrimidine (97% of theory) are obtained.

EXAMPLE 2

Per hour, 219 g of dimethylformamide, 306 g of phosgene and 301.5 g of vinyl isobutyl ether are passed into the first of a cascade of 3 stirred vessels. In each case, the overflow and the off-gas are fed into the liquid phase of the next stirred vessel. The reaction temperature is 65°C throughout and the total residence time of the liquid is about 5 hours. 684 g per hour of a homogeneous liquid product are obtained. This is reacted continuously with guanidine in the further stirred apparatuses, placed downstream from the above cascade. 2-Aminopryrimidine is obtained in a yield of 95% of theory.

We claim:

1. A process for the manufacture of a malondialdehyde derivative of the general formula

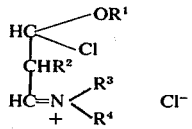

where $R^1$ is alkyl of up to 8 carbon atoms, $R^2$ is hydrogen or alkyl or alkoxy of up to 20 carbon atoms, and $R^3$ and $R^4$ are identical or different alkyl or, together with nitrogen to which they are attached, form a heterocyclic ring of up to 7 members, by reaction of phosgene with a dialkylformamide of the general formula

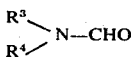

to give the dialkylformamide chloride and reaction of the dialkylformamide chloride with an enol ether (vinyl ether) of the general formula $R^2$—CH=CH—OR$^1$ $R^1$, $R^2$, $R^3$ and $R^4$ having the above meanings, in which process the reactions are allowed to take place simultaneously.

2. A process as claimed in claim 1, wherein the reactions are carried out continuously, at least 50% of the conversion being achieved in a reaction space which permits controllable back-mixing, and the remaining conversion (if any) being carried out in a reaction vessel in which essentially no back-mixing takes place.

3. A process as claimed in claim 1, wherein the reaction is carried out in the essentially complete absence of solvents which do not participate in the reaction.

* * * * *